United States Patent [19]

Clinton, deceased

[11] 4,304,791
[45] Dec. 8, 1981

[54] BENZENAMINES, FORMULATIONS, AND FUNGICIDAL METHOD

[75] Inventor: Albert J. Clinton, deceased, late of Indianapolis, Ind., by Thomas L. Plimpton for American Fletcher National Bank and Trust Company, special administrator

[73] Assignee: Eli Lilly and Company, Indianapolis, Ind.

[21] Appl. No.: 110,308

[22] Filed: Jan. 8, 1980

[51] Int. Cl.³ .................... C07C 87/60; C07C 87/62; A61K 31/04
[52] U.S. Cl. ................................ 424/330; 260/465 E; 560/21; 562/435; 564/433; 564/434; 424/304; 424/309; 424/319

[58] Field of Search ............... 424/330, 304, 309, 319; 260/571, 465 E; 560/21; 562/435; 564/433, 434

[56] References Cited

FOREIGN PATENT DOCUMENTS 156 1/1979 European Pat. Off. ............ 260/571
4642 10/1979 European Pat. Off. ............ 260/571

Primary Examiner—Robert Gerstl
Attorney, Agent, or Firm—Charles W. Ashbrook; Arthur R. Whale

[57] ABSTRACT

N-Nitrophenyl-(tetrafluoroethoxy)-benzenamines are useful as fungicides, anticoccidials and ectoparasiticides, in addition to being insecticidal agents.

33 Claims, No Drawings

BENZENAMINES, FORMULATIONS, AND FUNGICIDAL METHOD

BACKGROUND OF THE INVENTION

Benzenamines have experienced widespread usage in the field of agriculture. Numerous benzenamines are known which are effective as herbicidal agents. Among the most widely used herbicidal benzenamines are trifluralin, which is N,N-di-n-propyl-2,6-dinitro-4-trifluoromethylbenzenamine, butralin, which is N-(1-methylpropyl)2,6-dinitro-4-tert.-butylbenzenamine, and benefin, N-butyl-N-ethyl-2,6-dinitro-4-trifluoromethylbenzenamine.

Several bezenamines are known to be useful in animal health. For example, European Pat. No. 156, published Jan. 10, 1979, discloses various N-(2,4-dinitro-6-trifluoro-methylphenyl)benzenamines which are said to exhibit useful insecticidal, acaricidal, nematocidal, insect growth retardant, fungicidal and bactericidal activity. Similarly, antifungal benzenamines are disclosed in U.S. Pat. No. 4,152,460.

An object of the present invention is to provide certain novel N-(nitrophenyl)-polyfluoroethoxybenzenamines which are potent antifungal agents, and which also display ectoparasitic and anticoccidial activity.

SUMMARY OF THE INVENTION

This invention concerns benzenamines, formulations containing such compounds, and a method for treating soil and plant fungal diseases. The invention is more particularly directed to N-(nitrophenyl)-(tetra and penta fluoroethoxy)benzenamines defined by the general formula

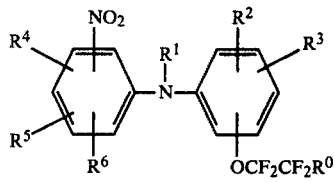

wherein:
$R^0$ is hydrogen or fluoro;
$R^1$ is hydrogen or $C_1$–$C_2$ alkyl;
$R^2$ and $R^3$ independently are hydrogen or halo;
$R^4$ is hydrogen, trifluoromethyl, cyano, $C_1$–$C_4$ alkyl, hydroxycarbonyl or $C_1$–$C_4$ alkoxycarbonyl;
$R^5$ is hydrogen, halo, nitro, hydroxy, methoxy or amino;
$R^6$ is hydrogen or nitro; and the physiologically-acceptable salts thereof.

Preferred compounds provided by this invention include those having the above formula wherein $R^6$ is nitro.

Especially preferred compounds comprehended by this invention are those of the formula

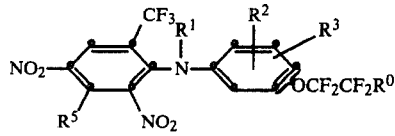

wherein:

$R^0$ is hydrogen or fluoro;
$R^1$ is hydrogen or $C_1$–$C_2$ alkyl;
$R^2$ and $R^3$ independently are hydrogen or halo;
$R^5$ is hydrogen or halo; and the physiologically-acceptable salts thereof.

Additionally preferred compounds are those wherein $R^2$ and $R^3$ are the same, $R^4$ is hydrogen, trifluoromethyl, cyano, $C_1$–$C_4$ alkyl, or hydroxycarbonyl; $R^5$ is chloro, bromo or nitro; and $R^6$ is nitro.

Another preferred group of benzenamines according to this invention have the above formula wherein $R^0$, $R^1$, $R^2$, $R^3$ and $R^5$ all are hydrogen, $R^4$ is trifluoromethyl and $R^6$ is nitro.

A further embodiment of this invention is a formulation comprising an N-(nitrophenyl)-polyfluoroethoxybenzenamine defined by the above general formula admixed with a suitable carrier, diluent or excipient therefor.

Also provided by this invention is a method for treating fungicidal infections in plants and in soil comprising applying to the locus to be treated an antifungal amount of a benzenamine defined by the above formula.

DETAILED DESCRIPTION OF THE INVENTION $R^1$ in the above formula defines hydrogen or $C_1$–$C_2$ alkyl, namely methyl or ethyl.

$R^2$, $R^3$ and $R^5$ include the groups referred to herein as "halo". The term bears its art-recognized meaning of fluoro, chloro, bromo and iodo. Preferred halo groups defined by $R^2$, $R^3$ and $R^5$ are chloro and bromo.

$R^4$ in the above formula includes $C_1$–$C_4$ alkyl groups, which are straight and branched chain alkyl group having from one to four carbon atoms. Typical $C_1$–$C_4$ alkyl groups include methyl, ethyl, n-propyl iso-propyl, n-butyl and tert.-butyl.

$R^4$ additionally defines a $C_1$–$C_4$ alkoxycarbonyl moiety, for instance methoxycarbonyl, ethoxycarbonyl, isopropoxycarbonyl, n-butoxycarbonyl, and related groups.

The N-nitrophenyl-(tetra and penta)fluoroethoxybenzenamines comprehended by this invention can be prepared by any of several chemical processes. A preferred and commonly utilized process involves the condensation reaction of a substituted phenyl electrophilic agent with a phenylamine derivative. For example, a polyfluoroethoxyphenyl electrophilic agent such as a phenyl halide can be condensed with a nitrophenylamine according to the following scheme:

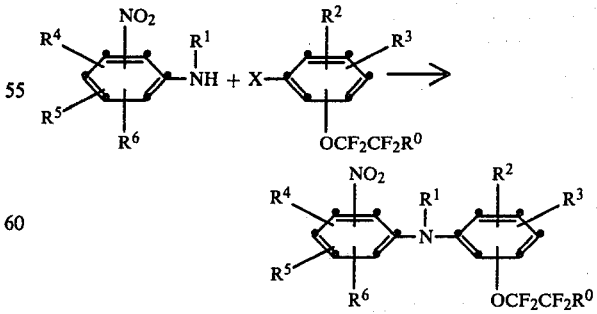

wherein $R^0$, $R^1$, $R^2$, $R^3$, $R^4$, $R^5$ and $R^6$ are as defined above, and X is a good leaving group such as halo, for instance chloro, bromo or iodo. A similar, yet alternative, process comprises condensing a nitrophenyl electrophilic agent with a polyfluoroethoxyphenylamine according to the following scheme:

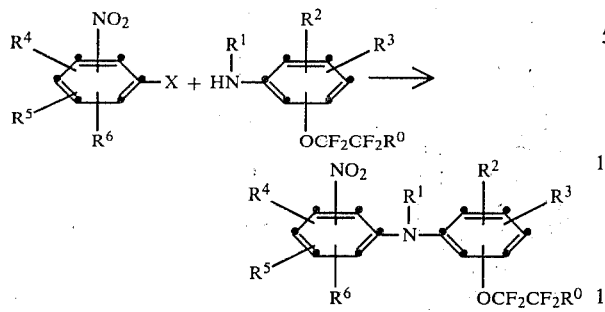

wherein $R^0$, $R^1$, $R^2$, $R^3$, $R^4$, $R^5$ and $R^6$ are as defined above, and X is a good leaving group such as halo. Such reactions are preferably carried out when $R^1$ is hydrogen.

According to the processes outlined above, a substituted phenyl electrophilic agent such as a tetra or pentafluoroethoxyphenyl chloride is mixed with about an equimolar quantity of a nitrophenylamine. The condensation reaction generally is carried out in an unreactive organic solvent and in the presence of a strong base. Commonly used unreactive organic solvents include amides, for instance dimethylformamide or hexamethylphosphortriamide; ethers such as tetrahydrofuran, diethyl ether, or dioxane; sulfoxides such as dimethyl sulfoxide; alcohols such as methanol or ethanol; and related solvents. Strong bases which may be utilized in the reaction include alkli metal hydrides, for instance sodium hydride or lithium hydride; amines such as triethylamine, pyridine, DBN (1,5-diazabicyclo [4.3.0]-non-5-ene) and DBU (1,5-diazabicyclo[5.4.0] undec-5-ene, carbonates such as potassium carbonate and sodium carbonate; alkoxides such as potassium tert.-butoxide, and the like.

The condensation reaction generally is carried out by first adding a phenylamine to a strong base in a suitable solvent. For instance, a phenylamine such as 3-(1,1,2,2-tetrafluoroethoxyphenyl)amine can be reacted with a base such as sodium hydride in a solvent such as dimethylformamide. The reactants can be employed in about equimolar quantities, or if desired an excess of base, for example about a 0.1 to about a 10 molar excess, can be utilized if desired. The phenylamine and the strong base generally are allowed to react for up to about 3 hours at a temperature of about $-30°$ to about $30°$ C., preferably about $0°$ to about $25°$ C. Following the initial reaction of the phenylamine and the strong base, the desired substituted phenyl electrophilic agent, for instance a compound such as 2,4-dinitro-6-trifluoromethylphenyl chloride, is added to the reaction mixture, and the reaction is permitted to continue for about 2 to about 48 hours at a temperature of about $0°$ to about $100°$ C.

The product of the condensation reaction is a compound comprehended by this invention and is readily isolated by simply adding the reaction mixture to an aqueous acid solution, for instance dilute aqueous hydrochloric acid or sulfuric acid. The desired product often precipitates out of the aqueous acid solution as a solid or an oil. Anternatively, the product may be extracted into a water immiscible organic solvent such as diethyl ether, ethyl acetate, dichloromethane, or the like. Removal of the organic solvent, for instance by evaporation under reduced pressure, then provides a compound of this invention. The product thus formed can be further purified if desired by any of several standard methods, including column chromatography over a solid support such as silica gel or the like, or crystallization from common solvents such as ethanol, benzene, skelly B, diethyl ether, acetone, and the like.

Certain benzenamines provided by this invention can be prepared by modification of an existing benzenamine prepared as described above. For example, N-alkylation of a benzenamine having the above formula wherein $R^1$ is hydrogen affords the corresponding benzenamine wherein $R^1$ is $C_1$–$C_2$ alkyl. Such alkylation reactions typically are accomplished by combining an alkylating agent with a benzenamine (wherein $R^1$ is hydrogen) is an unreactive organic solvent and in the presence of a base. Typical alkylating agents commonly used include alkyl halides such as methyl bromide or ethyl iodide, as well as sulfates such as dimethyl sulfate and diethyl sulfate. Commonly used solvents include acetone, benzene, methyl ethyl ketone, dimethylsulfoxide and the like. The alkylation routinely is substantially complete within about two to about seventy-two hours when carried out at a temperature of about $30°$ to about $150°$ C. The N-alkylated benzenamine is generally isolated by extraction of the reaction mixture with a solvent such as diethyl ether or benzene, and then evaporation of the solvent from the extract. The product can be further purified if desired by crystallization, chromatography, distillation, or related purification techniques.

Benzenamines bearing a carboxylic acid moiety, that is to say compounds of the above general formula wherein $R^4$ is hydroxycarbonyl, are readily esterified to provide benzenamines wherein $R^4$ is a $C_1$–$C_4$ alkoxy carbonyl group. Such conversion can be accomplished by standard esterification reactions. Methyl esters are often preferably prepared by simply reacting a free acid with diazomethane in a suitable solvent such as diethyl ether. Esterification can also be accomplished by condensing a benzenamine carboxylic acid with a $C_1$–$C_4$ alkanol in the presence of an acid, for instance sulfuric acid or the like. Alternatively, a benzenamine carboxylic acid can be converted to an acid halide, and the acid halide then can be condensed with a $C_1$–$C_4$ alkanol. For example, reaction of a benzenamine such as N-(2-nitro-4-hydroxycarbonylphenyl)-4-(1,1,2,2-tetrafluoroethoxy)benzenamine with oxalyl chloride affords N-(2-nitro-4-chlorocarbonylphenyl)-4-(1,1,2,2,-tetrafluoroethoxy)benzenamine, which when reacted with an alkanol such as isopropanol affords N-(2-nitro-4-isopropoxycarbonylphenyl)-4-(1,1,2,2-tetrafluoroethoxy)benzenamine.

Benzenamines having the above formula wherein one or both of $R^2$ and $R^3$ are hydrogen can be halogenated by reaction with a halogenating agent in a suitable solvent. For instance, a compound such as N-(2,6-dinitro-4-trifluoromethyl)-3-(1,1,2,2-tetrafluoroethoxy)benzenamine can be reacted with about one equivalent, or an excess if desired, of bromine in the presence of a solvent such as dichloromethane or a mixture of acetic acid and water. Such reaction effects bromination to provide, for instance, N-(2,6-dinitro-4-trifluoromethyl)-2,4-dibromo-5-(1,1,2,2-tetrafluoroethoxy)benzenamine.

When desired, the above described halogenation reaction can be carried out utilizing less than one molar quantity of halogenating agent, thereby effecting monohalogenation instead of dihalogenation. The monohalogenated product can be further halogenated if desired with the same or a different halogenating agent. For instance a benzenamine such as N-(2,6-dinitro-4-trifluoromethylphenyl)-3-(1,1,2,2,2-pentafluoroethoxy)-benzenamine can be reacted with about a 0.5 molar amount of chlorine in dichloromethane at about 25° C. to give N-(2,6-dinitro-4-trifluoromethylphenyl)-2-chloro-3-(1,1,2,2,2-pentafluoroethoxy)benzenamine. The latter compound can be further halogenated, for instance by reaction with about a 0.5 to 1.0 molar amount of bromine in dichloromethane, to provide the corresponding dihalogenated derivative, for example N-(2,6-dinitro-4-trifluoromethylphenyl)-2-chloro-4-bromo-5-(1,1,2,2,2-pentafluoroethoxy)benzenamine.

The benzenamines contemplated herein wherein $R^1$ is hydrogen are weakly acidic in nature by virtue of the activated proton attached to the amino nitrogen atom to which the two aromatic rings are attached. Because of this acidic nature, the benzenamines readily form physiologically-acceptable salts by reaction with any of a number of common inorganic and organic bases. The salts are in general solids and thus lend themselves to purification by crystallization from common solvents such as ethanol, acetone, ethyl acetate, methyl ethyl ketone, and the like.

The salts provided herein are prepared by reaction of about equimolar quantities of a benzenamine and a base. Inorganic bases commonly employed to form salts of this invention include the alkali metal hydroxides such as sodium hydroxide and potassium hydroxide, as well as alkali metal amides such as lithium amide and potassium amide. Routinely used organic bases include alkali metal alkoxides such as potassium tert.-butoxide and sodium methoxide, as well as alkali metal amides such as lithium or potassium diisopropylamide.

When it is desired to regenerate the free amine from an addition salt, the salt is simply reacted with an acid such as hydrochloric acid or sulfuric acid. For example, reaction of the sodium salt of N-(2,4-dinitrophenyl)-3-(1,1,2,2-tetrafluoroethoxy)benzenamine with about one equivalent amount of hydrochloric acid converts the salt to a free amine to provide N-(2,4-dinitrophenyl)-3-(1,1,2,2-tetrafluoroethoxy)benzenamine.

Representative benzenamines comprehended by this invention include the following:

N-(2,6-dinitro-4-trifluoromethylphenyl)-3-(1,1,2,2-tetrafluoroethoxy)benzenamine.

N-(2,6-dinitro-4-cyanophenyl)-2-(1,1,2,2-tetrafluoroethoxy)benzenamine;

N-(2,4-dinitro-6-trifluoromethylphenyl)-N-ethyl-4-(1,1,2,2-tetrafluoroethoxy)benzenamine;

N-(2,4-dinitro-6-hydroxycarbonylphenyl)-3-(1,1,2,2-tetrafluoroethoxy)-4-chlorobenzenamine;

N-(3-nitro-4-chlorophenyl)-N-methyl-4-(1,1,2,2-tetrafluoroethoxy)benzenamine;

N-(2-trifluoromethyl-4-nitrophenyl)-2-(1,1,2,2-tetrafluoroethoxy)benzenamine;

N-(3-trifluoromethyl-4-nitrophenyl)-N-methyl-3-(1,1,2,2-tetrafluoroethoxy)benzenamine;

N-(2,6-dinitro-4-ethoxycarbonylphenyl)-3-(1,1,2,2-tetrafluoroethoxy)-4,5-dichlorobenzenamine;

N-(2-nitrophenyl)-3-(1,1,2,2-tetrafluoroethoxy)benzenamine;

N-(2,4-dinitro-6-isopropyl)-N-ethyl-2,6-dichloro-4-(1,1,2,2-tetrafluoroethoxy)benzenamine;

N-(2,4,6-trinitrophenyl)-N-ethyl-3-(1,1,2,2-tetrafluoroethoxy)benzenamine;

N-(2,6-dinitro-3-bromo-4-trifluoromethylphenyl)-4-(1,1,2,2,2-pentafluoroethoxy)benzenamine;

N-(2-nitro-4-tert.-butylphenyl)-2,6-dibromo-4-(1,1,2,2-tetrafluoroethoxy)benzenamine;

N-(3,4-dinitrophenyl)-2-bromo-6-chloro-4-(1,1,2,2,2-pentafluoroethoxy)benzenamine;

N-(2,3,4-trinitro-5-methylphenyl)-2-(1,1,2,2-tetrafluoroethoxy)-3,5-dibromobenzenamine;

N-(2-nitro-4-ethoxycarbonylphenyl)-N-ethyl-3-(1,1,2,2-tetrafluoroethoxy)benzenamine;

N-(2,4-dinitro-6-n-butylphenyl)-2,6-dichloro-3-(1,1,2,2-tetrafluoroethoxy)benzenamine;

N-(2,6-dinitro-4-hydroxycarbonylphenyl)-3-(1,1,2,2-tetrafluoroethoxy)benzenamine;

N-(2,4-dinitro-6-hydroxycarbonylphenyl)2,6-difluoro-4-(1,1,2,2-tetrafluoro)benzenamine;

N-(2,4,6-trinitrophenyl)-N-methyl-2,4-diiodo-5-(1,1,2,2,2-pentafluoroethoxy)benzenamine;

Sodium N-(2-nitrophenyl)-3-(1,1,2,2,2-pentafluoroethoxy)benzenamide;

Potassium N-(2,6-dinitro-4-cyanophenyl)-2,6-dibromo-3-(1,1,2,2-tetrafluoroethoxy)benzenamide;

Lithium N-(2,4-dinitro-6-trifluoromethylphenyl)-3-(1,1,2,2-tetrafluoroethoxy)benzenamide;

Sodium N-(2,6-dinitro-4-trifluoromethylphenyl)-4-(1,1,2,2-tetrafluoroethoxy)benzenamide;

Lithium N-(2,4,6-trinitrophenyl)-2-(1,1,2,2-tetrafluoroethoxy)benzenamide;

N-(2-trifluoromethyl-5-chloro-4,6-dinitrophenyl)-4-(1,1,2,2-tetrafluoroethoxy)benzenamine;

N-(2,4-dinitro-6-hyroxycarbonylphenyl)-2,4-dibromo-5-(1,1,2,2-tetrafluoroethoxy)benzenamine;

Potassium N-(2,6-dinitro-4-trifluoromethyl)-3-bromo-4-(1,1,2,2-tetrafluoroethoxy)benzenamide;

Sodium N-(2-nitro-3-chloro-4-cyanophenyl)-2-(1,1,2,2-tetrafluoroethoxy)benzenamide;

N-(2,6-dinitro-4-trifluoromethylphenyl)-2,4-dichloro-5-(1,1,2,2,2-pentafluoroethoxy)benzenamine;

N-(2,4,6-trinitrophenyl)-3-(1,1,2,2,2-pentafluoroethoxy)benzenamine;

N-(2-trifluoromethyl-4-nitrophenyl)-3-(1,1,2,2,2-pentafluoroethoxy)benzenamine;

N-(2,4-dinitro-6-trifluoromethylphenyl)-N-ethyl-4-(1,1,2,2,2-pentafluoroethoxy)benzenamine; and the like.

The detailed examples which follow illustrate the preparation of representative compounds embraced by the present invention. The examples are representative only and should not be construed as limiting in any respect.

EXAMPLE 1

N-(2,4-dinitro-6-trifluoromethylphenyl)-4-(1,1,2,2-tetrafluoroethoxy)benzenamine To a stirred solution of 1.0 g. of 4-(1,1,2,2-tetrafluoroethoxy)phenylamine in 50 ml. of ethanol containing 3.0 ml. of triethylamine were added in one portion 1.3 g. of 2,4-dinitro-6-trifluoromethylphenyl chloride. The reaction mixture was heated at reflux for sixteen hours following the addition. The reaction mixture then was added to 100 ml. of ice water containing about 10 ml. of hydrochloric acid. The precipitate which formed was collected and dissolved in diethyl ether. The ethereal solution was washed with water and dried, and the solvent was removed by evaporation under reduced pressure to provide 1.2 g. of N-(2,4-dinitro-6-trifluoromethylphenyl)-4-(1,1,2,2-tetrafluoroethoxy)benzenamine.

Yield 54.9% M.P. 105°–107° C. Analysis calculated for $C_{15}H_8F_7N_3O_5$ Theory: C, 40.65; H, 1.82; N, 9.48. Found: C, 40.89; H, 2.08; N, 9.66.

EXAMPLE 2

N-(2,6-dinitro-4-tert.-butylphenyl)-4-(1,1,2,2-tetrafluoroethoxy)benzenamine

A solution of 2.5 g. of 4-(1,1,2,2-tetrafluoroethoxy)phenylamine hydrochloride in 30 ml. of ethanol containing 5.0 ml. of triethylamine and 2.6 g. of 2,6-dinitro-4-tert.-butylphenyl chloride was stirred and heated at reflux for sixteen hours. The reaction mixture was then slowly added to 100 ml. of ice water containing 10 ml. of concentrated hydrochloric acid, and the aqueous mixture was stirred for thirty minutes. The oil which formed was collected and crystallized from skelly-B solvent and diethyl ether to give 2.4 g. of N-(2,6-dinitro-4-tert.-butylphenyl)-4-(1,1,2,2-tetrafluoroethoxy)benzenamine.

Yield 51.3% M.P. 142°–143° C. Analysis calculated for $C_{18}H_{17}F_4N_3O_5$ Theory: C, 50.12; H, 3.97; N, 9.74. Found: C, 50.28; H, 4.02; N, 9.99.

EXAMPLES 3–12

Following the general procedure of Examples 1 and 2, the appropriate fluoroethoxyphenylamine was reacted with the appropriate nitrophenyl halide in the presence of triethylamine in ethanol to give the following benzenamines.

N-(2,6-dinitro-4-cyanophenyl)-4-(1,1,2,2-tetrafluoroethoxy)benzenamine.

Yield 89.3% M.P. 104°–106° C. Analysis calculated for $C_{15}H_8F_4N_4O_5$ Theory: C, 45.01; H, 2.01; N, 14.00. Found: C, 45.29; H, 1.95; N, 14.04.

N-(2,6-dinitro-4-hydroxycarbonylphenyl)-4-(1,1,2,2-tetrafluoroethoxy)benzenamine.

Yield 74.6% M.P. 234°–236° C. Analysis calculated for $C_{15}H_{11}N_3O_7$ Theory: C, 42.97; H, 2.16; N, 10.02. Found: C, 43.25; H, 2.36; N, 10.10.

N-(2,6-dinitro-3-chloro-4-trifluoromethylphenyl)-4-(1,1,2,2-tetrafluoroethoxy)benzenamine.

Yield 60.3% M.P. 127°–130° C. Analysis calculated for $C_{15}H_7ClF_7N_3O_5$ Theory: C, 37.70; H, 1.47; N, 8.80. Found: C, 37.95; H, 1.53; N, 8.59.

N-(2,4-dinitro-6-hydroxycarbonylphenyl)-4-(1,1,2,2-tetrafluoroethoxy)benzenamine.

Yield 50.0% M.P. 192°–195° C. Analysis calculated for $C_{15}H_8F_4N_3O_7$ Theory: C, 42.97; H, 2.16; N, 10.02. Found: C, 43.23; H, 2.30; N, 9.74.

N-(2,6-dinitro-4-tert.-butylphenyl)-3-(1,1,2,2-tetrafluoroethoxy)benzenamine.

M.P. 129°–131° C. Analysis calculated for $C_{18}H_{17}F_4N_3O_5$ Theory: C, 50.12; H, 3.97; N, 9.74. Found: C, 50.02; H, 3.89; N, 9.48.

N-(2,6-dinitro-4-trifluoromethylphenyl)-3-(1,1,2,2-tetrafluoroethoxy)benzenamine. (oil)

Analysis calculated for $C_{15}H_8F_7N_3O_5$ Theory: C, 40.65; H, 1.82; N, 9.48. Found: C, 40.91; H, 1.84; N, 9.24.

N-(2,4-dinitro-6-trifluoromethylphenyl)-3-(1,1,2,2-tetrafluoroethoxy)benzenamine.

M.P. 75°–76° C. Analysis calculated for $C_{15}H_7F_7N_3O_5$ Theory: C, 40.56; H, 1.82; N, 9.48. Found: C, 40.87; H, 2.02; N, 9.49.

N-(2,6-dinitro-4-trifluoromethylphenyl)-4-(1,1,2,2-tetrafluoroethoxy)benzenamine.

Yield 83.5% M.P. 102°–105° C. Analysis calculated for $C_{15}H_8F_7N_3O_5$ Theory: C, 40.65; H, 1.82; N, 9.48. Found: C, 40.82; H, 1.79; N, 9.63.

N-(2,4,6-trinitrophenyl)-4-(1,1,2,2-tetrafluoroethoxy)benzenamine.

M.P. 141°–142° C. Analysis calculated for $C_{14}H_8N_4O_7$ Theory: C, 40.01; H, 1.92; N, 13.33. Found: C, 40.17; H, 2.04; N, 13.09.

N-(2,4,6-trinitrophenyl)-3-(1,1,2,2-tetrafluoroethoxy)benzenamine.

M.P. 128°–129° C. Analysis calculated for $C_{14}H_8N_4O_7$ Theory: C, 40.01; H, 1.92; N, 13.33. Found: C, 40.14; H, 1.99; N, 13.44.

EXAMPLE 13

N-(2-trifluoromethyl-4-nitrophenyl)-3-(1,1,2,2-tetrafluoroethoxy)benzenamine

Two grams of a 50% suspension of sodium hydride in mineral oil were washed several times with pentane, and then suspended in 25 ml. of N,N-dimethylformamide. To the stirred mixture were added in one portion 3.8 g. of 3-(1,1,2,2-tetrafluoroethoxy)phenylamine. The reaction mixture was stirred at ambient temperature for thirty minutes, and then 4.5 g. of 2-trifluoromethyl-4-nitrophenylchloride were added dropwise over five minutes to the reaction mixture. The mixture was stirred for three hours at room temperature, and then added slowly to 100 ml. of dilute hydrochloric acid solution. An oil which precipitated was collected, dissolved in diethyl ether, and chromatographed over silica gel. After collecting the fractions shown by thin layer chromatography to contain a single product and evaporating the solvent therefrom, there were recovered, as an oil, 2.0 g of N-(2-trifluoromethyl-4-nitrophenyl)-3-(1,1,2,2-tetrafluoroethoxy)benzenamine.

Analysis calculated for $C_{15}H_9F_7N_3O_3$ Theory: C, 45.24; H, 2.28; N, 7.03. Found: C, 45.03; H, 2.24; N, 7.09.

EXAMPLES 14–17

N-(2,6-dinitro-4-trifluoromethylphenyl)-2-(1,1,2,2-tetrafluoroethoxy)benzenamine Analysis calculated for $C_{15}H_8F_7N_3O_5$ Theory: C, 40.65; H, 1.82; N, 9.48. Found: C, 40.85; H, 1.80; N, 9.48.

N-(2,4-dinitro-6-hydroxycarbonylphenyl)-2-(1,1,2,2-tetrafluoroethoxy)benzenamine.

Analysis calculated for $C_{15}H_9F_4N_3O_7$ Theory: C, 43.08; H, 1.93; N, 10.05. Found: C, 43.27; H, 2.01; N, 9.81.

N-(2,4,6-trinitrophenyl)-2-(1,1,2,2-tetrafluoroethoxy)benzenamine.

M.P. 114°–115° C. Analysis calculated for $C_{14}H_8F_4N_4O_7$ Theory: C, 40.01; H, 1.92; N, 13.33. Found: C, 39.88; H, 1.99; N, 13.62.

N-(2,4-dinitro-6-tert.-butylphenyl)-4-(1,1,2,2-tetrafluoroethoxy)benzenamine.

M.P. 98°–101° C. Analysis calculated for $C_{18}H_{17}F_4N_3O_5$ Theory: C, 50.12; H, 3.97; N, 9.74. Found: C, 50.24; H, 4.01; N, 9.86.

EXAMPLE 18

N-(2,4-dinitro-6-trifluoromethylphenyl)-N-methyl-3-(1,1,2,2-tetrafluoroethoxy)benzenamine.

A solution of 4.0 ml. of dimethyl sulfate in 30 ml. of acetone containing 5.0 g. of sodium carbonate and 3.0 g. of N-(2,4-dinitro-6-trifluoromethylphenyl)-3-(1,1,2,2-tetrafluoroethoxy)benzenamine was heated at reflux for sixteen hours. An additional 2.0 ml. of dimethyl sulfate was added to the reaction mixture, and refluxing was continued for an additional four hours. The reaction mixture was cooled to room temperature and diluted by the addition of 150 ml. of water. The aqueous mixture was stirred for thirty minutes, and then the product was extracted into diethyl ether. The ethereal extracts were combined, washed with water, dried, and the solvent was removed by evaporation under reduced pressure to provide 3.7 g. of an oil, identified as N-(2,4-dinitro-6-trifluoromethylphenyl)-N-methyl-3-(1,1,2,2-tetrafluoroethoxy)benzenamine.

Analysis calculated for $C_{16}H_7F_7N_3O_5$ Theory: C, 42.03; H, 2.20; N, 9.19. Found: C, 42.24; H, 2.34; N, 9.32.

EXAMPLE 19

Following the procedure of Example 18, N-(2,4-dinitro-6-trifluoromethylphenyl)-4-(1,1,2,2-tetrafluoroethoxy)benzenamine was reacted with dimethyl sulfate and sodium carbonate in acetone to provide N-(2,4-dinitro-6-trifluoromethylphenyl)-N-methyl-4-(1,1,2,2-tetrafluoroethoxy)benzenamine.

M.P. 91°-92° C. Analysis calculated for $C_{16}H_7F_7N_3O_5$ Theory: C, 42.03; H, 2.20; N, 9.19. Found: C, 42.27; H, 2.06; N, 9.43.

EXAMPLE 20

N-(2,4-dinitro-6-trifluoromethylphenyl)-N-methyl-2,4-dibromo-5-(1,1,2,2-tetrafluoroethoxy)-benzenamine.

To a stirred solution of 1.5 g. of N-(2,4-dinitro-6-trifluoromethylphenyl)-N-methyl-3-(1,1,2,2-tetrafluoroethoxy)benzenamine in 30 ml. of acetic acid containing 10 ml. of water were added in one portion 1.5 ml. of bromine. The reaction mixture was stirred for three hours at room temperature, and then was diluted by the addition of 30 ml. of water. The mixture was stirred for an additional one hour, and then the solvent was decanted to leave a solid precipitate. The solid was dissolved in diethyl ether, dried, and the solvent was removed by evaporation under reduced pressure to afford 1.8 g. of N-(2,4-dinitro-6-trifluoromethylphenyl)-N-methyl-2,4-dibromo-5-(1,1,2,2-tetrafluoroethoxy)benzenamine.

M.P. 97°-99° C. Analysis calculated for $C_{16}H_8Br_2F_7N_3O_5$ Theory: C, 31.25; H, 1.31; N, 6.83. Found: C, 31.26; H, 1.38; N, 6.92.

EXAMPLES 21-22

Following the procedure of Example 20, a halogen was reacted with a benzenamine to give the following halogenated benzenamines:

N-(2,4-dinitro-6-trifluoromethylphenyl)-2,6-dichloro-4-(1,1,2,2-tetrafluoroethoxy)benzenamine.

M.P. 80°-82° C. Analysis calculated for $C_{15}H_6Cl_2F_7N_3O_5$ Theory: C, 35.18; H, 1.18; N, 8.21. Found: C, 35.48; H, 1.31; N, 8.50.

N-(2,4-dinitro-6-trifluoromethylphenyl)-2,6-dibromo-4-(1,1,2,2-tetrafluoroethoxy)benzenamine.

M.P. 92°-93° C. Analysis calculated for $C_{15}H_6Br_2F_7N_3O_5$ Theory: C, 29.98; H, 1.01; N, 6.99. Found: C, 30.12; H, 1.05; N, 7.17.

EXAMPLE 23

N-(2,4,6-trinitrophenyl)-2,4-dibromo-5-(1,1,2,2-tetrafluoroethoxy)benzenamine

To a stirred solution of 1.7 g. of N-(2,4,6-trinitrophenyl)-3-(1,1,2,2-tetrafluoroethoxy)benzenamine in 20 ml. of dichloromethane were added in one portion 1.5 ml. of bromine. The reaction mixture was heated at reflux for sixteen hours, and then 1.0 ml. of bromine was added. The mixture was refluxed for an additional two hours, and then cooled to room temperature. The precipitate which formed was collected by filtration to provide 1.4 g. of N-(2,4,6-trinitrophenyl)-2,4-dibromo-5-(1,1,2,2-tetrafluoroethoxy)benzenamine.

M.P. 201°-203° C. Analysis calculated for $C_{14}H_5Br_2F_4N_4O_7$ Theory: C, 29.09; H, 1.05; N, 9.69. Found: C, 29.35; H, 0.96; N, 9.81.

EXAMPLES 24-26

Various benzenamines were halogenated in dichloromethane by the procedure of Example 23 to give the following halo substituted benzenamines:

N-(2,6-dinitro-4-trifluoromethylphenyl)-2,4-dichloro-5-(1,1,2,2-tetrafluoroethoxy)benzenamine.

M.P. 142°-143° C. Analysis calculated for $C_{15}H_6Cl_2F_7N_3O_5$ Theory: C, 35.18; H, 1.18; N, 8.21. Found: C, 35.48; H, 1.19; N, 8.12.

N-(2,6-dinitro-4-trifluoromethylphenyl)-2,4-dibromo-5-(1,1,2,2-tetrafluoroethoxy)benzenamine.

M.P. 161°-163° C. Analysis calculated for $C_{15}H_6Br_2F_7N_3O_6$ Theory: C, 29.98; H, 1.01; N, 6.99. Found: C, 30.04; H, 1.18; N, 7.14.

N-(2,4-dinitro-6-trifluoromethylphenyl)-2,4-dibromo-5-(1,1,2,2-tetrafluoroethoxy)benzenamine. (oil)

Analysis calculated for $C_{15}H_6Br_2F_7N_3O_5$ Theory: C, 36.94; H, 1.77; N, 9.24. Found: C, 37.24; H, 2.05; N, 9.55.

As hereinbefore pointed out, the compounds of this invention have several utilities, including plant and soil antifungicidal activity. In a further embodiment of this invention, there are provided formulations for use in treating plant and soil fungicidal infections. Such formulations comprise a benzenamine of the above formula admixed with a suitable carrier, diluent or excipient therefor.

As used herein, the term "carrier", "diluent" or "excipient" refers to a material or materials with which the above-described benzenamine can be mixed or formulated to facilitate its storage, transport, handling, and administration to animals or application to plants or soil. Such carriers, diluents and excipients can be solid or liquid, and are preferably substantially inert chemically and biologically. Commonly used solid carriers for use in dust formulations include gypsum, tripolite, diatomaceous earth, mineral silicates, vermiculite, talc, clays, calcium and magnesium limes, calcite and related solid substances. Solid waxes, polymers and copolymers can be employed if desired. Typical liquid carriers include water, saline, or organic fluids such as oils, for example a horticultural petroleum product.

The formulations comprehended by this invention comprise a suitable carrier, diluent or excipient admixed with a benzenamine of the above formula. The formulations will contain from about 5 to about 90 percent by weight of a benzenamine provided by this invention. A preferred concentration of active ingredient is from about 20 to about 80 percent by weight. The combinations can take the form of concentrates, for instance aqueous emulsions or the like, or as sprays, dry powders, wettable powders, and the like. Preferred formulations include wettable powders, which are solid compositions of matter wherein the benzenamine is absorbed or adsorbed in or on a sorptive carrier such as finely divided clay, talc, gypsum, lime, wood flour, kieserlguhr or the like. Wettable powder formulations commonly contain a small amount of a wetting, dispersing or emulsifying agent to facilitate dispersion in water or other liquid carriers utilized to distribute the active ingredient to the locus of desired fungus control. Commonly used wetting agents include condensed aryl sulfonic acids and sodium salts thereof, alkyl aryl polyether alcohols, sulfonated nonionic blends, anionic wetting agents, and the like.

Other preferred formulations according to this invention are emulsifiable concentrates, which are homogenous liquid or paste compositions of benzenamines which readily disperse in water or other liquid carrier to make a liquid which facilitates application to the locus of desired fungus control. Typical emulsifiable concentrates will contain a benzenamine of the above formula admixed with an organic solvent such as xylene, heavy aromatic naphthas, dioxane, or dimethylformamide, in addition to one or more emulsifying agents such as phenols, polyoxyethylene derivatives of sorbitan esters, complex ether-alcohols, and the like. Other ingredients such as antifreezes, antifoaming agents, stabilizers, antibacterial agents and the like can be utilized if desired.

Examples 27 and 28 which follow illustrate typical formulations contemplated herein.

EXAMPLE 27

| Wettable Powder Formulation | |
|---|---|
| Ingredient | Percent by Weight |
| N-(2-trifluoromethyl-5-chloro-4,6-dinitrophenyl)-4-(1,1,2,2-tetrafluoroethoxy)-benzenamine | 25.8 |
| Stepanol Me } Wetting and | 5.0 |
| Polyfon O } dissipating agents | 5.0 |
| Zeolex-7 | 10.0 |
| Bardens Clay | 54.2 |

The above ingredients are mixed and air milled to provide a finely divided uniform powder. The powder is dispersed in water at the site of application and sprayed on the locus where fungal control is desired. The rate of application is about 5 to about 30 pounds of active ingredient per acre.

EXAMPLE 28

| Emulsifiable Concentrate Formulation | |
|---|---|
| Ingredient | Percent by Weight |
| N-(2,6-dinitro-4-trifluoromethylphenyl)-2,4-dichloro-5-(1,1,2,2-tetrafluoroethoxy)-benzenamine | 43.5 |
| Orthochlorotoluene | 18.5 |
| Ethoxylated polyoxypropylene glycol surfactant (atlox 8916TF) | 5.0 |
| Propylene glycol | 1.0 |
| Water | 33.0 |

The above ingredients are combined to form an aqueous emulsion which is to be diluted by additional water at the site of application. Such diluted formulation will be applied to the soil to be treated at a rate such that the active ingredient is about 10 to about 20 pounds per acre.

The compounds provided by this invention have several utilities, including ectoparasitic activity, insecticidal activity, anticoccidial activity, as well as antifungal activity. A further embodiment of this invention is a method for treating and controlling fungal diseases in soil and on growing plants. The benzenamines defined by the above general formula can be applied as a drench to soil and incorporated therein prior to the emergence of plant seedlings, or can alternatively be applied to the foilage of growing plants such as cotton, beans, including soybeans and the like. The compounds are effective against a number of plant pathogenic fungi when applied pre- or post-emergent at rates of about 0.1 to about 50 pounds per acre, ideally about 10 to about 20 pounds per acre. The compounds are effective in controlling and treating several common fungal diseases, including those caused by pathogens of the species Rhizoctonia, Fusarium (root rot), Verticillium (wilt), Pythium and the like.

A number of the compounds provided herein have been evaluated as antifungal agents in standard greenhouse tests. In a typical test, a benzenamine of this invention was formulated by mixing 70 mg. of the compound with 2 ml. of a solution comprising 500 ml. of ethanol, 500 ml. of acetone, and 100 ml. of Tween 20 (a polyoxyethylene sorbitan monolaurate made by Atlas Chemical Division of ICI America, Inc., Wilmington, Delaware). The mixture thus formed was diluted with 175 ml. of deionized water containing one drop of antifoam C emulsion per 2 liters of water. The final formulation contained 400 ppm. of benzenamine test compound, 10,000 ppm. of organic solvents, and 1,000 ppm. of Tween 20. This solution was diluted with deionized water to obtain desired lower concentrations of active ingredient.

On the day a test was initiated, young expanding leaves of plants were detached and placed bottom side up in petri dishes containing filter paper placed on top of an expanding plastic mat to keep the leaves above the water flooding the bottom of the dishes. A water-soaked wad of cotton was wrapped around the petriole base of the leaf. The test chemical at the desired concentration was sprayed on the underside of the leaves to run off and the leaves were then allowed to dry. The dried leaves were inoculated by spraying with a suspension of pathogenic fungi using a DeVilbiss sprayer. After inoculation, the dishes were placed in a moist chamber. The leaves were observed for disease symptoms and the results were recorded seven days after treatment. A rating scale of 1 to 5 was used to record the results, in which scale "1" equals severe disease, "2" equals moderately severe disease, "3" equals moderate disease, "4" equals slight disease and "5" equals no disease.

The results of such test is presented in Table I which follows. Column A in the table identifies the benzenamine evaluated. Column B gives the application rate in parts per million (ppm). Column C lists the rating of control against each of the indicated species of fungal infection.

TABLE I

| A<br>Compound Tested | B<br>Application<br>Rate<br>(ppm) | C<br>Disease Species and<br>Control Rating | |
|---|---|---|---|
| N-(2,6-dinitro-4-trifluoromethylphenyl)-N-methyl-3-(1,1,2,2-tetrafluoroethoxy)-benzenamine | 400 | Powdery Mildew<br>Rice Blast<br>Wheat Leaf Rust | 1<br>4<br>1 |

TABLE I-continued

| A<br>Compound Tested | B<br>Application<br>Rate<br>(ppm) | C<br>Disease Species and<br>Control Rating | |
|---|---|---|---|
| N-(2,4-dinitro-6-trifluoro-methylphenyl)-2,4-dibromo-5-(1,1,2,2-tetrafluoroethoxy)-benzenamine | 400 | Powdery Mildew<br>Rice Blast<br>Wheat Leaf Rust | 3<br>5<br>4 |
| N-(2-trifluoromethyl-4-nitro-phenyl)-3-(1,1,2,2-tetrafluoro-ethoxy)benzenamine | 400 | Powdery Mildew<br>Anthracnose<br>Rice Blast | 1<br>3<br>1 |
| N-(2,6-dinitro-4-trifluoro-methylphenyl)-2,4-dichloro-5-(1,1,2,2-tetrafluoroethoxy)-benzenamine | 400 | Powdery Mildew<br>Rice Blast<br>Wheat Leaf Rust | 1<br>1<br>1 |

Compounds of this invention have additionally been evaluated in soil disease tests to demonstrate their antifungal activity. Test compounds were formulated by dissolving 57 mg. of compound in 1 ml. of a fifty percent (V/V) solution of acetone and ethanol. A 0.1% aqueous solution of Tween 20 was added to bring the final volume to 16 ml.

Pathogen-infested soil was placed in 8 oz. paper cups. A depression was made in the surface of the soil and 3 g. of Celatom MP-78 granules were placed in the depression. A 4 ml. aliquot of chemical formulation was added to the granules, and the cups were then covered with lids. The containers are shaken by hand for about 10 seconds, and then placed on a roller for about 10 minutes to thoroughly incorporate the test chemical into the soil. The treated soil was transferred to a 2.5 inch round plastic pot, and seeds of the host plant were added, and covered with additional treated soil. The effect of the test compounds was observed on the growing plants and was rated on a scale of 1 to 5 (1 is severe disease, 5 is no disease). The results of such evaluations are presented in Table II. Column A lists the compounds evaluated. Column B lists the application rates in pounds per acre (lbs/ac). Column C records the plant variety. Column D lists the pathogen and the disease rating for the tested compound.

TABLE II

| A<br>Compound Evaluated | B<br>Application Rate<br>(lbs./A) | C<br>Plant Variety | D<br>Disease Rating | |
|---|---|---|---|---|
| N-(2,4-dinitro-6-trifluoro-methylphenyl)-3-(1,1,2,2-tetrafluoroethoxy)benzenamine | 40 | Cotton | Rhizoctonia | 5 |
| | 40 | Cotton | Rhizoctonia | 4 |
| | 20 | Cotton | Rhizoctonia | 5 |
| | 10 | Cotton | Rhizoctonia | 5 |
| | 40 | Cotton | Pythium | 1 |
| | 40 | Beans | Fusarium | 1 |
| | 40 | Cotton | Verticillium | 1 |
| N-(2,4-dinitro-6-trifluoro-methylphenyl)-2,4-dibromo-5-(1,1,2,2-tetrafluoroethoxy)-benzenamine | 40 | Cotton | Rhizoctonia | 5 |
| | 40 | Cotton | Rhizoctonia | 5 |
| | 20 | Cotton | Rhizoctonia | 5 |
| | 10 | Cotton | Rhizoctonia | 5 |
| | 10 | Cotton | Rhizoctonia | 5 |
| | 5 | Cotton | Rhizoctonia | 3 |
| | 2.5 | Cotton | Rhizoctonia | 3 |
| | 40 | Beans | Fusarium | 1 |
| | 40 | Cotton | Verticillium | 1 |
| N-(2,6-dinitro-4-trifluoro-methylphenyl)-2,4-dichloro-3-(1,1,2,2-tetrafluoroethoxy)-benzenamine | 40 | Cotton | Rhizoctonia | 1 |
| | 40 | Cotton | Pythium | 1 |
| | 40 | Beans | Fusarium | 4 |
| | 40 | Beans | Fusarium | 3 |
| | 20 | Beans | Fusarium | 3 |
| | 10 | Beans | Fusarium | 3 |
| | 40 | Cotton | Verticillium | 1 |
| N-(2-trifluoromethyl-4-nitro-phenyl)-3-(1,1,2,2-tetrafluoro-ethoxy)benzenamine | 40 | Cotton | Rhizoctonia | 4 |
| | 40 | Cotton | Rhizoctonia | 4 |
| | 20 | Cotton | Rhizoctonia | 3 |
| | 10 | Cotton | Rhizoctonia | 3 |
| | 40 | Cotton | Pythium | 4 |
| | 40 | Cotton | Pythium | 3 |
| | 20 | Cotton | Pythium | 3 |
| | 10 | Cotton | Pythium | 1 |
| | 40 | Beans | Fusarium | 4 |
| | 40 | Beans | Fusarium | 4 |
| | 20 | Beans | Fusarium | 4 |
| | 10 | Beans | Fusarium | 4 |
| | 40 | Cotton | Verticillium | 1 |
| N-(2,4,6-trinitrophenyl)-2,4-dibromo-5-(1,1,2,2-tetrafluoroethoxy)benzen-amine | 40 | Cotton | Rhizoctonia | 1 |
| | 40 | Cotton | Pythium | 1 |
| | 40 | Cotton | Verticillium | 1 |
| | 40 | Beans | Fusarium | 1 |
| N-(2,4-dinitro-6-trifluoro-methylphenyl)-N-methyl-3-(1,1,2,2-tetrafluoroethoxy)-benzenamine | 40 | Cotton | Rhizoctonia | 2 |
| | 40 | Cotton | Pythium | 3 |
| | 40 | Beans | Fusarium | 1 |
| | 40 | Cotton | Verticillium | 5 |
| | 40 | Cotton | Verticillium | 1 |
| | 20 | Cotton | Verticillium | 1 |
| | 10 | Cotton | Verticillium | 1 |

The data thus presented in Tables I and II demonstrate that the compounds of this invention can be used to control or treat diseases occurring in soil and plants and caused by pathogenic fungi. A further embodiment of this invention accordingly is an antifungal method which comprising applying to the locus to be treated an antifungal amount of a benzenamine of this invention. As already noted, the compounds can be formulated in any of a number of ways to facilitate convenient application to soil or to growing plants. The compounds are preferably applied as a liquid spray or drench, or alternatively as a dust or granule. While the specific rate of application of benzenamine may vary depending upon the disease to be treated, the host plant, the soil conditions of moisture and texture, the typical rate of application for field use will be about 0.1 to about 50 pounds per acre, and more preferably about 10 to about 20 pounds per acre.

The benzenamines of this invention have also demonstrated good anticoccidial activity and good ectoparasitic activity. For example, N-(2,4-dinitro-6-trifluoromethylphenyl)-3-(1,1,2,2-tetrafluoroethoxy)benzenamine demonstrated complete control of adult housefly and blowfly larva in standard tests designed to show ectoparasitic activity. Compounds such as N-(2,4-dinitro-3-chloro-6-trifluoromethylphenyl)-4-(1,1,2,2-tetrafluoroethoxy)benzenamine and N-(2,4-dinitro-3-bromo-6-trifluoromethylphenyl)-4-(1,1,2,2,2-pentafluoroethoxy)benzenamine are contemplated as excellent insecticidal and anticoccidial agents.

I claim:

1. A compound of the formula

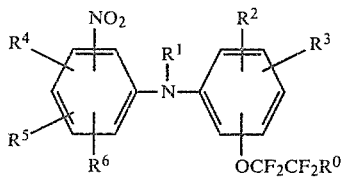

wherein:
$R^0$ is hydrogen;
$R^1$ is hydrogen or $C_1$–$C_2$ alkyl;
$R^2$ and $R^3$ independently are hydrogen or halo;
$R^4$ is hydrogen, trifluoromethyl, cyano, $C_1$–$C_4$ alkyl, hydroxycarbonyl, or $C_1$–$C_4$ alkoxycarbonyl;
$R^5$ is hydrogen, halo, nitro, hydroxy, methoxy or amino;
$R^6$ is hydrogen or nitro; and the physiologically-acceptable salts thereof.

2. The compound of claim 1 wherein $R^6$ is nitro.

3. The compound of claim 2 wherein $R^2$ and $R^3$ are the same and are hydrogen or halo.

4. The compound of claim 3 wherein $R^4$ is hydrogen, trifluoromethyl, cyano, $C_1$–$C_4$ alkyl or hydroxycarbonyl.

5. The compound of claim 4, wherein $R^5$ is chloro, bromo or nitro.

6. The compound of claim 5, said compound being N-(2,4,6-trinitrophenyl)-3-(1,1,2,2-tetrafluoroethoxy)-benzenamine.

7. The compound of claim 5, said compound being N-(2,4,6-trinitrophenyl)-2,4-dibromo-5-(1,1,2,2-tetrafluoroethoxy)benzenamine.

8. The compound of claim 5, said compound being N-(2-trifluoromethyl-5-chloro-4,6-dinitrophenyl)-4-(1,1,2,2-tetrafluoroethoxy)benzenamine.

9. The compound of claim 4 wherein $R^5$ is hydrogen.

10. The compound of claim 9, said compound being N-(2,4-dinitro-6-trifluoromethylphenyl)-2,4-dibromo-5-(1,1,2,2-tetrafluoroethoxy)benzenamine.

11. The compound of claim 9, said compound being N-(2,6-dinitro-4-trifluoromethylphenyl)-2,4-dibromo-5-(1,1,2,2-tetrafluoroethoxy)benzenamine.

12. The compound of claim 9, said compound being N-(2,6-dinitro-4-trifluoromethylphenyl)-2,4-dichloro-5-(1,1,2,2-tetrafluoroethoxy)benzenamine.

13. The compound of claim 9, said compound being N-(2,6-dinitro-4-tert.-butylphenyl)-4-(1,1,2,2-tetrafluoroethoxy)benzenamine.

14. The compound of claim 9, said compound being N-(2,6-dinitro-4-hydroxycarbonylphenyl)-4-(1,1,2,2-tetrafluoroethoxy)benzenamine.

15. The compound of claim 9, said compound being N-(2,6-dinitro-4-cyanophenyl)-4-(1,1,2,2-tetrafluoroethoxy)benzenamine.

16. The compound of claim 9, said compound being N-(2,4-dinitro-6-trifluoromethylphenyl)-N-methyl-3-(1,1,2,2-tetrafluoroethoxy)benzenamine.

17. The compound of claim 9, said compound being N-(2,4-dinitro-6-trifluoromethylphenyl)-N-methyl-4-(1,1,2,2-tetrafluoroethoxy)benzenamine.

18. The compound of claim 9, said compound being N-(2,4-dinitro-6-trifluoromethylphenyl)-N-methyl-2,4-dibromo-5-(1,1,2,2-tetrafluoroethoxy)benzenamine.

19. The compound of claim 2, wherein $R^1$, $R^2$, $R^3$ and $R^5$ are hydrogen, $R^4$ is trifluoromethyl and $R^6$ is nitro.

20. The compound of claim 19, said compound being N-(2,4-dinitro-6-trifluoromethylphenyl)-4-(1,1,-2,2-tetrafluoroethoxy)benzenamine.

21. The compound of claim 19, said compound being N-(2,4-dinitro-6-trifluoromethylphenyl)-2-(1,1,-2,2-tetrafluoroethoxy)benzenamine.

22. The compound of claim 19, said compound being N-(2,4-dinitro-6-trifluoromethylphenyl)-3-(1,1-2,2-tetrafluoroethoxy)benzenamine.

23. The compound of claim 19, said compound being N-(2,6-dinitro-4-trifluoromethylphenyl)-3-(1,1-2,2-tetrafluoroethoxy)benzenamine.

24. The compound of claim 19, said compound being N-(2,6-dinitro-4-trifluoromethylphenyl)-4-(1,1-2,2-tetrafluoroethoxy)benzenamine.

25. The compound of claim 1 having the formula

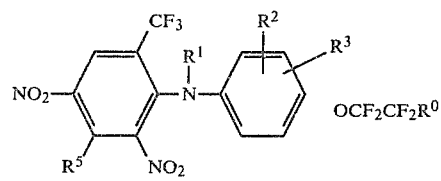

wherein:
$R^0$ is hydrogen;
$R^1$ is hydrogen or $C_1$–$C_2$ alkyl;
$R^2$ and $R^3$ independently are hydrogen or halo;
$R^5$ is hydrogen or halo; and the physiologically-acceptable salts thereof.

26. A formulation useful in the treatment of fungal infections in soil and on plants comprising an antifungal amount of a compound of claim 1 and a suitable carrier therefor.

27. The formulation of claim 26 comprising a compound of the formula

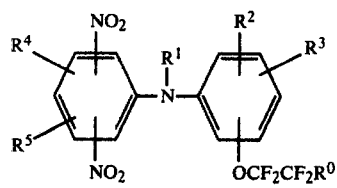

wherein:
R⁰ is hydrogen;
R¹ is hydrogen or $C_1$–$C_2$ alkyl;
R² and R³ independently are hydrogen or halo;
R⁴ is hydrogen, trifluoromethyl, cyano, $C_1$–$C_4$ alkyl, hydroxycarbonyl, or $C_1$–$C_4$ alkoxycarbonyl;
R⁵ is hydrogen, halo or nitro; and the physiologically-acceptable salts thereof.

28. The formulation of claim 27, wherein in the active ingredient, R² and R³ are the same, R⁴ is trifluoromethyl, cyano, $C_1$–$C_4$ alkyl or hydroxycarbonyl; and R⁵ is hydrogen.

29. The formulation of claim 28 wherein the active ingredient has the formula

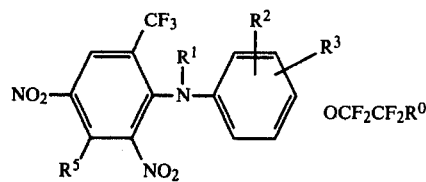

wherein:
R⁰ is hydrogen;
R¹ is hydrogen or $C_1$–$C_2$ alkyl;
R² and R³ independently are hydrogen or halo;
R⁵ is hydrogen or halo; and the physiologically-acceptable salts thereof.

30. A method for treating plant and soil fungal infections comprising applying to the locus to be treated an antifungal amount of a compound of claim 1.

31. The method of claim 30 wherein in the active compound applied, R⁶ is nitro.

32. The method of claim 31 wherein in the active compound applied, R² and R³ are the same; R⁴ is hydrogen, trifluoromethyl, cyano, $C_1$–$C_4$ alkyl, or hydroxycarbonyl; and R⁵ is chloro, bromo or nitro.

33. The method of claim 31 wherein in the active compound applied, R¹, R², R³ and R⁵ all are hydrogen, and R⁴ is trifluoromethyl.

* * * * *